United States Patent [19]
Wilson et al.

[11] Patent Number: 5,770,359
[45] Date of Patent: *Jun. 23, 1998

[54] RECOMBINANT DNA SEQUENCES, VECTORS CONTAINING THEM AND METHOD FOR THE USE THEREOF

[75] Inventors: Richard Harris Wilson, Glasgow, Scotland; Christopher Robert Bebbington, Windsor, England

[73] Assignees: Celltech Therapeutics Limited, Berkshire; The University Court of the University of Glasgow, Glasgow, both of England

[*] Notice: The term of this patent shall not extend beyond the expiration date of Pat. No. 5,122,464.

[21] Appl. No.: 302,241

[22] Filed: Sep. 8, 1994

Related U.S. Application Data

[63] Continuation of Ser. No. 165,533, Dec. 13, 1993, abandoned, which is a continuation of Ser. No. 852,390, Mar. 16, 1992, abandoned, which is a continuation of Ser. No. 595,733, Oct. 10, 1990, Pat. No. 5,122,464, which is a continuation of Ser. No. 117,071, filed as PCT/GB87/00039 Jan. 23, 1987, abandoned.

[30] Foreign Application Priority Data

Jan. 23, 1986 [GB] United Kingdom .................... 8601597

[51] Int. Cl.$^6$ ............................. C12Q 1/68; C12N 15/85; C12N 5/10; C07H 21/04
[52] U.S. Cl. .......................... 435/6; 435/325; 435/320.1; 435/358; 435/372.1; 536/23.2; 536/23.5
[58] Field of Search ............................... 435/69.1, 172.1, 435/172.3, 320.1, 240.2, 6, 325, 358, 372.1, 183; 536/23.5, 23.1, 23.2

[56] References Cited

U.S. PATENT DOCUMENTS

| | | | |
|---|---|---|---|
| 4,399,216 | 8/1983 | Axel et al. .................................... | 435/6 |
| 4,656,134 | 4/1987 | Ringold ..................................... | 435/91 |
| 4,797,359 | 1/1989 | Finkelstein .............................. | 435/69.1 |
| 5,122,464 | 6/1992 | Wilson et al. ........................ | 435/172.3 |

FOREIGN PATENT DOCUMENTS

WO8606409 4/1986 WIPO .............................. C12P 21/00

OTHER PUBLICATIONS

Alberts et al. "Molecular Biology of the Cell", Garland Publishing Inc., New York, 1983, pp. 184–193.

Watson et al. "Recombinant DNA, A Short Course" W.H. Freeman and Co., 1983, pp. 50–90.

Sanders, Peter G. et al., "Amplification and cloning of the Chinese hamster glutamine synthetase Gene", *EMBO*, vol. 3, No. 1, pp. 65–71 (1984).

Pennica, Diane et al., "Cloning and expression of human tissue–type plasminogen activator cDNA in *E. coli*", *Nature*, vol. 301, pp. 214–221 (1983).

Donn, Gunter et al., "Herbicide–Resistant Alfalfa Cells: An Example of Gene Amplification in Plants", *Journal of Molecular and Applied Genetics*, 2:621–635 (1984).

Young, Anthony P. et al., "Mouse 3T6 Cells That Overproduce Glutamine Synthetase", *The Journal of Biological Chemistry*, vol. 258, No. 18, pp. 11260–11266 (1983).

de Saint Vincent, Bruno Robert et al., "The Cloning and Reintroduction into Animal Cells of a Functional CAD Gene, a Dominant Amplifiable Genetic Marker" Cell, vol. 27, pp. 267–277 (1981).

Murray, Mark J. et al., "Construction and Use of a Dominant . . . ", *Molec. and Cell Biol.*, vol. 3, No. 1, pp. 32–43 (1983).

Kaufman, Randal J., et al., "Selection and Amplification of Heterologous Genes . . . ", *Proc.Natl. Acad.Sci. U.S.A.*, vol. 83, pp. 3136–3140 (1986).

Kabak, David B. et al., "Ribosomal DNA Magnification in Saccharomyces cerevisiae", *Bacteriol*, vol. 134, pp. 237–245 (1978).

Vel'Kov, V.V., "Amplification of Genes in Prokaryotic and Eukaryotic Systems", *Soviet Genetics*, vol. 18, pp. 348–396 (1982).

*Primary Examiner*—David Guzo
*Attorney, Agent, or Firm*—Spencer & Frank

[57] ABSTRACT

Recombinant DNA sequences which encode the complete amino acid sequence of a glutamine synthetase, vectors containing such sequences, and methods for their use, in particular as dominant selectable markers, for use in co-amplification of non-selected genes and in transforming host cell lines to glutamine independence are disclosed.

12 Claims, 12 Drawing Sheets

FIG. 2a

```
        1        10        20        30        40        50        60        70
a: --CCGAGCCGAGAATGGGAGTAGAGCCGACTGCTTGATTCCCACACCAATCTCCTCGCCGCTCTCACTTCG
        ----    >>>>>>>>>>>>>>>>>    >>>>    <<<<    <<<<<<    <<<

80        90       100       110       120       130       140
a: CCTCGTTCTCGTGGCTCGTGGCCCTGTCCACCCCGTCCATCATCCCGCGGCCACCGCTCAGAGCACCTTCCACC
   <<  <<<<<<<<<<  >>>>>>    >>>                         <<<<<<  <<  <<

150       160       170       180       190       200       210       220
a: ATGGCCACCTCAGCAAGTTCCCACTTGAACAAAACATCAAGAAATGTACTTGTGCCTGCCCCAGGGTGAGAAA
b:  M   A   T   S   A   S   S   H   L   N   K   N   I   K   Q   M   Y   L   C   L   P   Q   G   E   K
c: AcA  T   S   A   S   S   H   L   B   K   g   I   K   Z   m   Y   v   m   a   L   P   Q   Q   d   K
d: CB X-D                                                              CB XI-B
         1                           5                          10                          15                        20

230       240       250       260       270       280       290
a: GTCCAAGCCATGTATATCTGGGTTGATGGTACTGGAGAAGGACTGCGCTGCAAAACCCGCACCCTGGACTGTGAG
b:  V   Q   A   M   Y   I   W   V   D   G   T   G   E   G   L   R   C   K   T   R   T   L   D   C   E
c:  V   Q   A   M   Y   I   W   i   D   G   T   G   E   G   L   R   C   K   T   R   T   L   X   s   X
d:             CB VII
        25                          30                          35                          40                        45

300       310       320       330       340       350       360       370
a: CCCAAGTGTGTAGAAGAGTTACCTGAGTGGAATTTTGATGGCTCTAGTACCTTTCAGTCTGAGGGCTCCAACAGT
b:  P   K   C   V   E   E   L   P   E   W   N   F   D   G   S   S   T   F   Q   S   E   G   S   N   S
c:  P   K   p   a   s   t   n   l   z   r                   D   G   S   S   T   F   Q   S   E   G   S   N   S
        50                          55                          60                          65                        70
```

FIG.2b

```
       380         390         400         410         420         430         440
a: GACATGTATCTCAGCCCTGTTGCCATGTTTCGGGACCCCTTCCGCAGAGATCCCAACAAGCTGGTGTTCTGTGAA
b:  D   M   Y   L   S   P   V   A   M   F   R   D   P   P   F   R   R   D   P   P   N   K   L   V   F   C   E
c:  M   Y   L   v   P   a   A   M   F   R   D   P   P   F   k   R   D   P   P   N   X   L   V   F   C   E
d: CB XII-C                              CB VI-C
       75                        80                        85                        90                        95

450         460         470         480         490         500         510         520
a: GTTTTCAAGTACAACCGGAAGCCTGCAGAGACCAATTTAAGGCACTCGTGTAAACGGATAATGGACATGGTGAGC
b:  V   F   K   Y   N   R   K   P   A   E   T   N   L   R   H   S   C   K   R   I   M   D   M   V   S
c:  V   F   X   Y   N   X   k   r   P   A   E   T   N   L   X   X   X   t   C                    M   B   M   V   S
d:                                                                                CB XIV CB XII-C
       100                       105                       110                       115                       120

530         540         550         560         570         580         590
a: AACCAGCACCCCTGGTTTGGAATGGAACAGGAGTATACTCTGATGGGAACAGATGGGCACCCCTTTTGGTTGGCCT
b:  N   Q   H   P   W   F   G   M   E   Q   E   Y   T   L   M   G   T   D   G   H   P   F   G   W   P
c:  N   X   P   X   F   G   M   E   Q   M   E   Q   Y   T   L   M   G   T   r   G   P   P   F   G   X   P
d:               CB XII-A                                             CB VI-D
       125                       130                       135                       140                       145

600         610         620         630         640         650         660         670
a: TCCAATGGCTTTCCTGGGCCCCAAGGTCCGTATTACTGTGGTGTGGGCGCAGACAAAGCCTATGGCAGGGATATC
b:  S   N   G   F   P   G   P   Q   G   P   Y   Y   C   G   V   G   A   D   K   A   Y   G   R   D   I
c:  S   N   X   F   X   G   P   Q   a                P   Y   Y   C   G   V   G   A   D   K   A   Y   G   R   D   I
       150                       155                       160                       165                       170
```

FIG. 2c

```
a: GTGGAGGCTCACTACCGCGCCCTGCTTGTATGCTGGGGTCAAGATTACAGGAACAAATGCTGAGGTTCATGCCTGCC
b:  V  E  A  H  Y  R  A  C  L  Y  A  G  V  K  I  T  G  T  N  A  E  V  M  P  A
c:           A  C  L  Y  A  G  i  k                 g  G  T  N  X  X  V  M  P  A
d:        T VII-G                                    - CB VI-D              CB XI-H
        175              180              185              190              195 a: CAGTGGGAATTCCAAATAGGACCCCTGTGAAGGAATCCGCATGGGAGATCATCTCTGGGTGGCCCGTTTCATCTTG
b:  Q  W  E  F  Q  I  G  P  C  E  G  I  R  M  G  D  H  L  W  V  A  R  F  I  L
c:  Q  W  E  F  Q  I  G  P  C  E  G  I  d  M
        200              205              210              215              220 a: CATCGAGTATGTGAAGACTTTGGGGTAATAGCAACCTTTGACCCCAAGCCCATTCCTGGGAACTGGAATGGTGCA
b:  H  R  V  C  E  D  F  G  V  I  A  T  F  D  P  K  P  I  P  G  N  W  N  G  A
        225              230              235              240              245 a: GGCTGCCATACCAACTTTAGCACCAAGGCCATGCGGGAGGAGAATGGTCTGAAGCACATCGAGGAGGCCATCGAG
b:  G  C  H  T  N  F  S  T  K  A  M  R  E  E  N  G  L  K  H  I  E  E  A  I  E
c:                                M  X  E  E  N  G  L  K  Y  I  E  E  A  I  E
d:                                    CB III-C
        250              255              260              265              270
```

FIG. 2d

```
        980       990      1000      1010      1020      1030      1040
a: AAACTAAGCAAGCGGCACCGGTACCACATTCGAGCCTACGATCCCAAGGGGCCTGGACAATGCCCGTGGTCTG
b:  K  L  S  K  R  H  R  Y  H  I  R  A  Y  D  P  K  G  G  L  D  N  A  R  G  L
c:  X  L  St Ks n  i  n  y  q              A  Y  B  P  K
d:    T IX-B-2                                T IX-B-1
   275                280                285                290                295

1050      1060      1070      1080      1090      1100      1110      1120
a: ACTGGGTTCCACGAAACGTCCAACATCAACGACTTTTCTGCTGGTGTCGCCAATGCCAGCATCCGCATT
b:  T  G  F  H  E  T  S  N  I  N  D  F  S  A  G  V  A  N  R  S  A  S  I  R  I
c:              T  S  N  I  N  Y  q                        g  A  S  I  R  I
d:            (-CB III-C)                                         T IX-C-1
   300                305                310                315                320

1130      1140      1150      1160      1170      1180      1190
a: CCCCGGACTGTCGGCCAGGAGAAGAAAGGTTACTTTGAAGACCGCCGCCCCTCTGCCAATTGTGACCCCTTTGCA
b:  P  R  T  V  G  Q  E  K  K  G  Y  F  E  D  R  R  P  S  A  N  C  D  P  F  A
c:  P  R
d: T IX-E
   325                330                335                340                345

1200      1210      1220      1230      1240      1250      1260      1270
a: GTGACAGAAGCCATCGTCCGCACATGCCTTCTCAATGAGAACTGGCGACGAGCCCTTCCAATACAAAAACTAATTA
b:  V  T  E  A  I  V  R  T  C  L  L  N  E  T  G  D  E  P  F  Q  Y  K  N  ***
c:                 T  C  L  L  N  Z  T  G  B  Z  P  F  Q  Y  K
d:              T VI-K
   350                355                360                365                370  372
```

```
      1280      1290      1300      1310      1320      1330      1340
a: GACTTTGAGTGATCTTGAGCCCTTTCCTAGTTCATCCCACCCCCGCCCCAGCTGTCTCATTGTAACTCAAAGGATGG 1350      1360      1370      1380      1390      1400      1410      1420
a: AATATCAAGGTCTCTTTTTATTCCTCCGTGCCTCGTGCCCAGTTAATCTTGCTTTTATTGGTCAGAATAGAGGAGTCAAGTTCTT
e: AATATCAAGGTCTCTTTTTATTCCCTCGTGCCCAAAAAAAAAAAAAAAAAAAAAAAAAA
```

FIG.2e

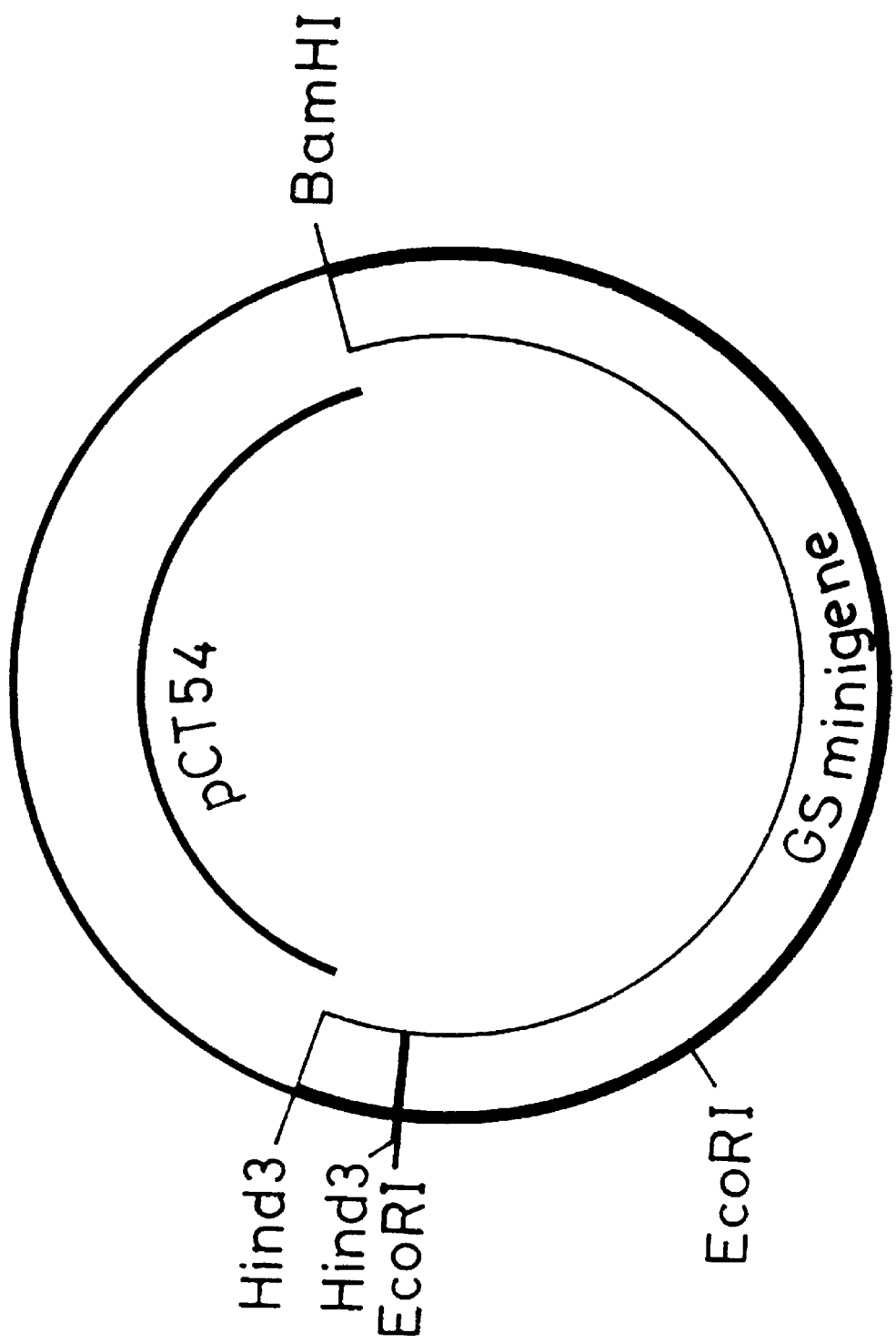

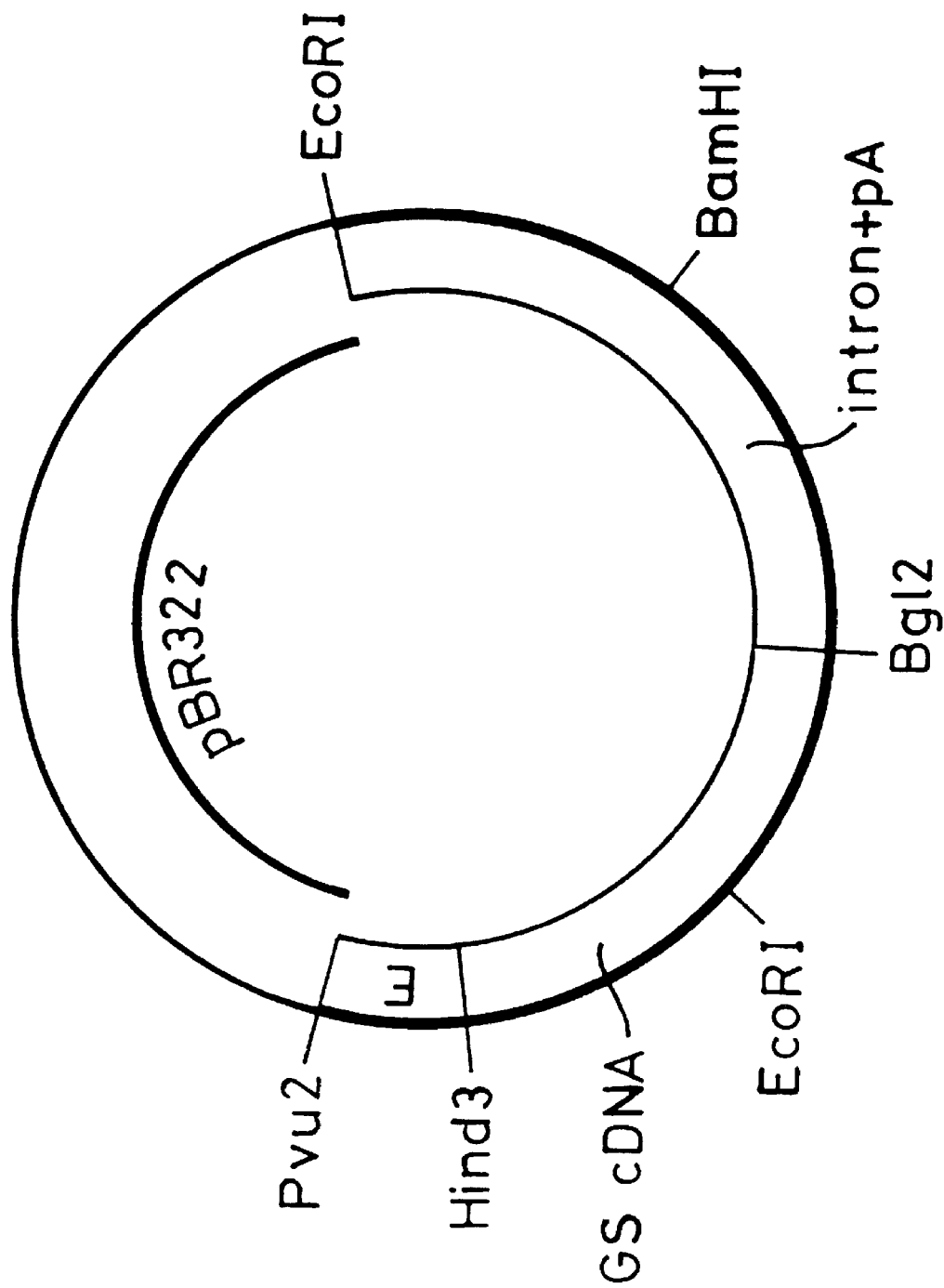
FIG. 3b pSV2.GS

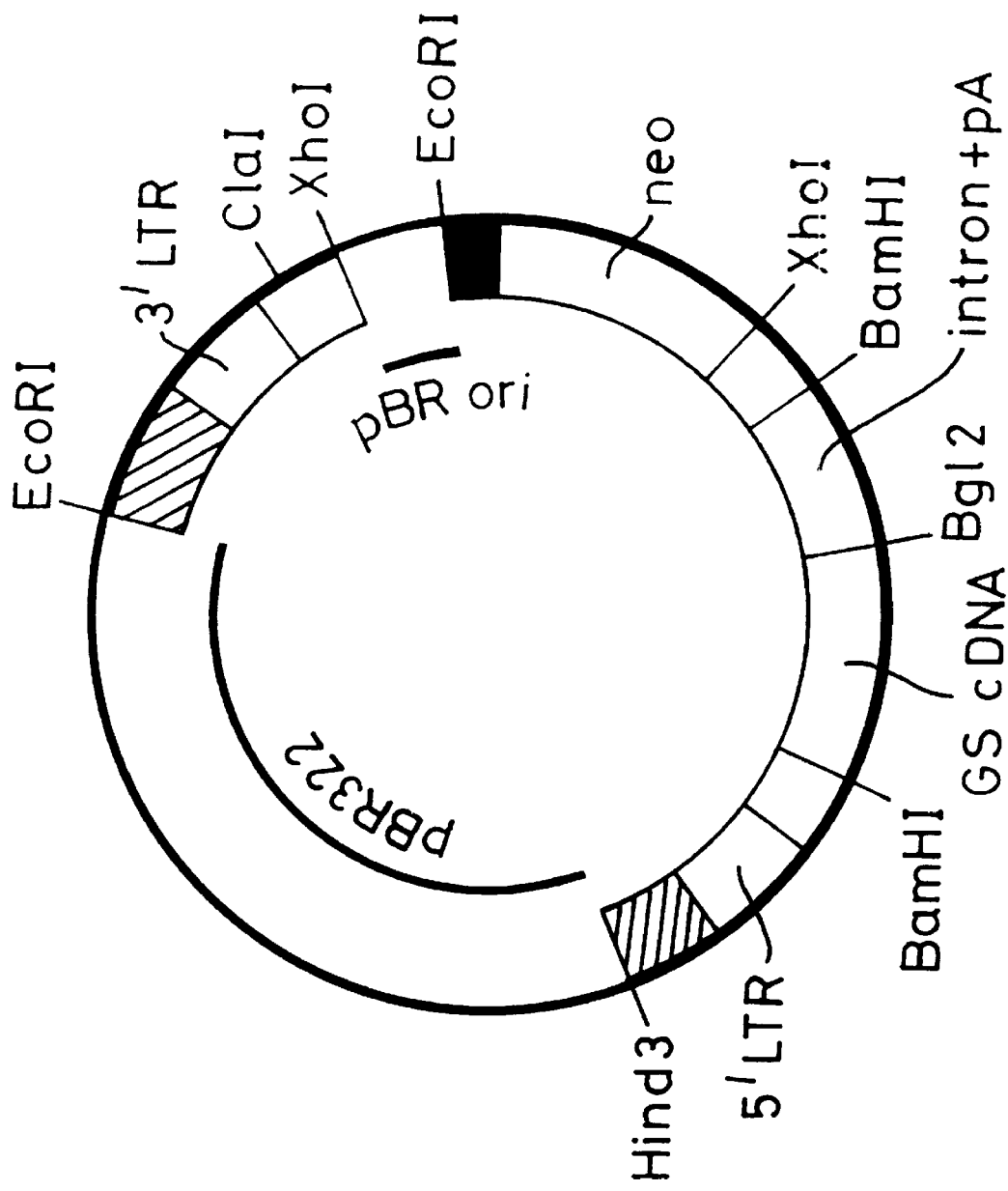
FIG. 3c pZIPGS

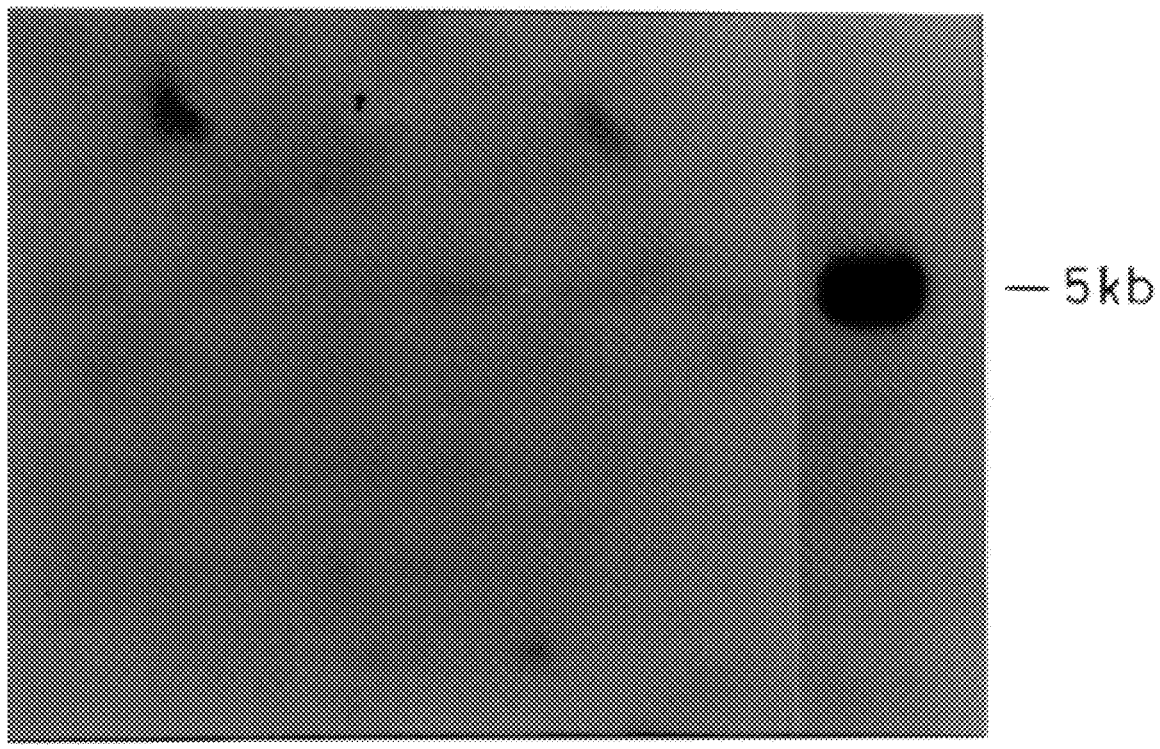

RECOMBINANT DNA SEQUENCES, VECTORS CONTAINING THEM AND METHOD FOR THE USE THEREOF

This application is a continuation application of Ser. No. 08/165,533, filed Dec. 13, 1993, abandoned which is a continuation of application Ser. No. 07/852,390 filed Mar. 16, 1992 abandoned which is a continuation of application Ser. No. 07/595,733 filed Oct. 10, 1990, which issued Jun. 16, 1992 as U.S. Pat. No. 5,122,464, which a continuation of application Ser. No. 07/117,071, filed as PCT/GB87/00039, Jan. 23, 1987, now abandoned.

The present invention relates to recombinant DNA sequences, vectors containing them and a method for the use thereof. In particular, the present invention relates to recombinant DNA sequences which encode the complete amino acid sequence of a glutamine synthetase (GS) (L-glutamate:ammonia ligase [ADP-forming]; EC 6.3.1.2) and to the use of such nucleotide sequences.

The ability of cloned genes to function when. introduced into host cell cultures has proved to be invaluable in studies of gene expression. It has also provided a means of obtaining large quantities of proteins which are otherwise scarce or which are completely novel products of gene manipulation. It is advantageous to obtain such proteins from mammalian cells since such proteins are generally correctly folded, appropriately modified and completely functional, often in marked contrast to those proteins as expressed in bacterial cells.

Where large amounts of product are required, it is necessary to identify cell clones in which the vector sequences are retained during cell proliferation. Such stable vector maintenance can be achieved either by use of a viral replicon or as a consequence of integration of the vector into the host cell's DNA.

Where the vector has been integrated into the host cell's DNA, the copy number of the vector DNA, and concomitantly the amount of product which could be expressed, can be increased by selecting for cell lines in which the vector sequences have been amplified after integration into the host cell's DNA.

A known method for carrying out such a selection procedure is to transform a host cell with a vector comprising a DNA sequence which encodes an enzyme which is inhibited by a known drug. The vector may also comprise a DNA sequence which encodes a desired protein. Alternatively the host cell may be co-transformed with a second vector which comprises the DNA sequence which encodes the desired protein.

The transformed or co-transformed host cells are then cultured in increasing concentrations of the known drug hereby selecting drug-resistant cells. It has been found that one common mechanism leading to the appearance of mutant cells which can survive in the increased concentrations of the otherwise toxic drug is the over-production of the enzyme which is inhibited by the drug. This most commonly results from increased levels of its particular mRNA, which in turn is frequently caused by amplification of vector DNA and hence gene copies.

It has also been found that, where drug resistance is caused by an increase in copy number of the vector DNA encoding the inhibitable enzyme, there is a concomitant increase in the copy number of the vector DNA encoding the desired protein in the host cell's DNA. There is thus an increased level of production of the desired protein.

The most commonly used system for such co-amplification uses as the enzyme which can be inhibited dihydrofolate reductase (DEFR). This can be inhibited by the drug methotrexate (MTX). To achieve co-amplification, a host cell which lacks an active gene which encodes DHFR is either transformed with a vector which comprises DNA sequences encoding DHFR and a desired protein or co-transformed with a vector comprising & DNA sequence encoding DEFR and a vector comprising a DNA sequence encoding the desired protein. The transformed or co-transformed host cells are cultured in media containing increasing levels of MTX, and those cell lines which survive are selected.

Other systems for producing co-amplification have been employed. However, none of them has been as widely used as the DHFR/MTX system.

The co-amplification systems which are at present available suffer from a number of disadvantages. For instance, it is generally necessary to use a host cell which lacks an active gene encoding the enzyme which can be inhibited. This tends to limit the number of cell lines which can be used with any particular co-amplification system. For instance, there is at present only one cell line known which lacks the gene encoding DEFR. It would be advantageous if an effective co-amplification system based on a dominant selectable marker which was applicable to a wide variety of cell lines could be provided. This would allow exploitation of different processing and growth characteristics of a variety of cell lines.

Attempts to use DHFR genes as dominant selectable markers in other cell lines has not proved entirely satisfactory. For instance, a MTX-resistant mutant DHFR or a DHFR gene under the control of a very strong promoter can act as a dominant selectable marker in certain cell types but such high concentrations of MTX are required that it has not been possible to achieve very high copy numbers by selection for gene amplification.

Co-transformants with an additional selectable marker also have disadvantages. For instance, this can increase the complexity of plasmid construction and requires additional time-consuming screening of transformed cells to distinguish those clones in which the DHFR gene is active.

A further disadvantage of the known co-amplification systems is that the DNA sequence encoding the inhibitable enzyme is generally not under post-translational control. The enzyme in the amplified system is therefore produced in large quantities, together with the desired protein. This could lead to lower levels of production of the desired protein.

Another disadvantage of known co-amplification systems is that resistance to the known drug can arise from mechanisms other than amplification. For instance, in the DHFR/MTX system, it is possible for a mutant DHFR gene to arise which produces a mutant DHFR which has a lower binding affinity for MTX than does wild-type DHFR. If such mutant DHFR arises, cells containing the gene which encodes it will be more resistant to MTX than the original host cell and will therefore be selected, even though no amplification has taken place. It is possible to select further to eliminate lines in which no amplification has taken place, but this is a time consuming process.

A further disadvantage of previous selection systems for gene amplification is that toxic drugs are required. In particular MTX is a potential carcinogen.

An additional disadvantage of previous amplification systems is the reed for repeated, time-consuming rounds of amplification, for example three or more, to obtain maximum copy number.

It is an object of the present invention to overcome at least in part the disadvantages of the prior art systems for co-amplification.

According to a first aspect of the present invention there is provided a recombinant DNA sequence which encodes the complete amino acid sequence of a glutamine synthetase (GS).

Typically, the recombinant DNA sequence encodes an eukaryotic, preferably mammalian, GS. Conveniently, the recombinant DNA sequence encodes a rodent, such as mouse, rat or especially hamster, GS.

Preferably, the recombinant DNA has the sequence of the amino acid coding portion of the sequence shown in FIG. 2, and most preferably comprises the whole recombinant DNA sequence shown in FIG. 2.

The recombinant DNA sequence of this aspect of the invention includes such a sequence from one species which hybridises under high strirgency conditions with another recombinant DNA sequence of this aspect of the invention or a part thereof from. a different species.

Glutamine synthetase (GS) is a universal housekeeping enzyme responsible for the synthesis of glutamate and ammonia using the hydrolysis of ATP to ADP and phosphate to drive the reaction. It is involved in the integration of nitrogen metabolism with energy metabolism via the TCA cycle, glutamine being the major respiratory fuel for a wide variety, possible the majority, of cell types.

GS is found at a low levels (0.01%–0.1% of soluble protein) in most higher vertebrate cells and is found at higher levels (>1% of total protein) in certain specialised cell types such as hepatocytes, adipocytes and glial cells.

A variety of regulatory signals affect GS levels within cells, for instance glucocorticoid steroids and cAMP, and glutamine in a culture medium appears to regulate GS levels post-translationally via ADP ribosylation.

GS from all sources is subject to inhibition by avariety of inhibitors, for example methionine sulphoximine (Msx). This compound appearing to act as a transition state analogue of the catalytic process. Extensively amplified GS genes have been obtained (Wilson R. H., Heredity, 49, 181, (1982); and Young A. P. and Ringold G. M., J. Biol. Chem., 258, 11260–11266, 1983) in variants of certain mammalian cell lines selected for Msx resistance. Recently Sanders and Wilson (Sanders P. G. and Wilson R. H., The EMBO Journal, 3, 1, 65–71, 1984) have described the cloning of an 8.2 kb BglII fragment containing DNA coding for GS from the genome of an Msx resistant Chinese hamster ovary (CHO) cell line KGIMS. However this fragment does not appear to contain a complete GS gene and it was not sequenced.

Conveniently, the recombinant DNA sequence of this aspect of the invention is cDNA, preferably derived by reverse transcription. However, the recombinant DNA sequence may alternatively or additionally comprise a fragment of genomic DNA.

It will be appreciated that, in accordance with the present invention, a recombinant DNA sequence of the first aspect, or a fragment thereof, may be used as a hybridization probe for obtaining GS coding sequences from other species.

Moreover the recombinant DNA sequences of the first aspect of the present invention may be used in medical or diagnostic methods, such as for detecting disease states in which the level of GS in a subject is altered.

However, it is envisaged that the main use of the recombinant DNA sequences of the first aspect of the present invention will be in co-amplification or dominant selectable marker systems employed in recombinant DNA technology.

Therefore according to a second aspect of the present invention, there is provided a recombinant DNA vector comprising a recombinant DNA sequence according to the first aspect of the invention.

Preferably, the vector is an expression vector capable, in a transformant host cell, of expressing the GS-encoding recombinant DNA sequence.

The vector may further comprise a recombinant DNA sequence which encodes the complete amino acid sequence of a desired protein other than GS. In the preferred case, the vector will also be capable, in the transformant host cell, of expressing the desired protein-encoding recombinant DNA sequence.

Preferably, the GS-encoding recombinant DNA sequence is under the control of a regulatable promoter, such as a heat shock or a metallothionein promoter.

The present invention also provides a host cell transformed with a vector according to the second aspect of the invention.

The vectors according to the second aspect of the present invention may be used in the co-amplification of non-selected genes. Therefore according to a third aspect of the present invention, there is provided a method for co-amplifying a recombinant DNA sequence which encodes the complete amino acid sequence of a desired protein other than GS which comprises:

either co-transforming a host cell with a vector according to the second aspect of the invention which does not contain a sequence encoding the desired protein, and a second vector comprising said desired protein-encoding recombinant DNA sequence;

or transforming the host cell with a vector according to the second aspect of the present invention which also includes a recombinant DNA sequence encoding the desired protein.

There are a number of advantages to the use of the vectors according to the present invention in co-amplification of non-selected genes.

An advantage is that the GS gene is regulatable, for instance by addition of glutamine to the medium. It is therefore possible to amplify the GS gene and the non-selected gene, and thendown-regulate the GS gene. The host cell will then accumulate much smaller quantities of active GS while still producing desirably large quantities of the required product. This also has the advantage of increasing the stability of the cell line, since there will be less selection pressure which could otherwise lead to instability in maintenance of amplified sequences in the cell line if the inhibitor is removed.

Cell lines are known which lack the GS gene. Moreover, there are available schemes whereby such cell lines may be selected. These GS deficient cell lines may be used in the co-amplification procedures.

However, it has been surprisingly and unexpectedly shown that GS expression vectors can also be used as effective dominant selectable markers in cell lines which contain an active GS gene by conferring resistance to certain levels of Msx at which the frequencies of resistance caused by endogeneous gene amplification is minimal. It has been shown that such vectors can be amplified by increasing the concentration of Msx in the cell lines so that high copy numbers are achieved. These copy numbers are higher than achieved using previous amplification systems such as DBFR/MTX, and are achieved in only two rounds of amplification. The possibility of attaining very high copy numbers is advantageous in ensuring that high levels of mRNA encoding the desired protein are obtained.

It is believed, although the Applicants do not wish to be limited by this theory, that the effectiveness of GS as an amplifiable dominant selectable marker is a consequence of the relative expression levels of endogeneous- and vector-derived GS genes. Selection for gene amplification using Msx leads almost exclusively to the isolation of clones in which the vector-derived GS gene has been amplified in preference to the endogeneous gene. When using host cells containing an endogeneous active GS gene, it is possible to facilitate selection by reducing or abolishing endogeneous GS activity, for instance by treatment of the cell line with dibutyryl-cAMP and theophylline. A cell line which is susceptible to such reduction or abolition is the 3T3-L1 cell line.

The desired protein whose recombinant DNA sequence is co-amplified may be, for instance, tissue plasminogen activator (tPA), although this technique can be used to co-amplify recombinant DNA sequences which encode any other protein, such as immunoglobulin polypeptides (IGs), human growth hormone (hGH) or tissue inhibitor of metalloproteinases (TIMP)

Preferably, the amplification is achieved by selection for resistance to progressively increased levels of a GS inhibitor, most preferably phosphinothricin or Msx.

A further advantage of the present co-amplification procedure is that Msx is a cheaply available product of high solubility. It can therefore readily be used at high concentrations to enable selection of lines containing highly amplified sequences.

Moreover, the effect of Msx can be potentiated by the addition to the selection medium of methionine. It is therefore preferred that in the present co-amplification procedure, selection is carried out in a medium containing methionine at higher than usual levels. Similarly, the effect of Msx can be potentiated by lower levels than usual of glutamate.

If the GS-encoding recombinant DNA sequence in the vector used for co-amplification is under the control of a regulatable promoter it is preferable for expression of the GS sequence to be switchedon during selection and amplification and subsequently down-regulated.

In some cases, after co-amplification, the selected cell line May be dependent to some extent on the GS inhibitor used in the selection procedure. If this is the case, the amount of GS inhibitor required may be reduced by adding glutamine to the culture medium whereby GS activity is post-translationally suppressed.

According to a fourth aspect of the present invention, a vector according to the second aspect of the invention way be used to provide a dominant selectable marker by transforming a host cell with the vector, thereby conferring transformant cells with resistance to GS inhibitors.

The host cells which are used in the fourth aspect of the present invention may contain an active GS gene. For the reasons set out above, it has been found that selection can still be achieved even where an active endogeneous gene is present. The advantages of using the vector of the present invention in co-amplification procedures are also shown in the use of the vectors as dominant selectable markers.

It is preferred that the host cells used for the co-amplification procedures or selection for dominant marker procedures of the present invention are mammalian, most preferably hamster, cells, and chinese hamster ovary (CEO)-KI cells or derivatives thereof are particularly suitable.

According to a fifth aspect of the present invention, the vectors according to the second aspect of the invention can be used in endowing a cell line with the ability to survive in a medium lacking glutamine by transforming a host cell completely lacking or reduced in GS activity an active GS gene with the vector. It is envisaged that this procedure will be particularly, but not exclusively, applicable to hybridoma and myeloma cells and derivatives thereof.

It has been found that the density to which certain cells, in particular myeloma cells, can grow in a medium may be limited by the requirement for glutamine or by-products of glutamine metabolism. If the cells could be made glutamine-independent either directly or as a result of additional medium alterations, it is believed that greater cell densities in culture could be achieved, thereby increasing the amount of protein produced per culture volume by the cell line.

It is therefore believed that the use of recombinant DNA sequences encoding GS, for instance in vectors for co-amplification, selection or transformation to glutamine independence, will lead to highly flexible and advantageous systems which will be surprisingly superior to other similar systems, for instance based on DHFR/MTX.

The present invention is now described, by way of example only, with reference to the accompanying drawings, in which:

BRIEF DESCRIPTION OF THE DRAWINGS

FIG. 2 (divided into FIGS. 2a, 2b, 2c, 2d, 2e for ease of illustration) shows the cDNA (a:) and predicted amino acid (b:) sequences for the Chinese hamster GS gene, together with the published peptide sequences (c:) and peptide designations (d:) of bovine brain GS. The sequence (e:) indicates the polyadenylation site Used in λgs 1.1. Amino acidresidues are indicated as their single letter codes; non-homologous bovine residues are indicated in lower case letters. The 'Λ' below base 7 represents the start of the pGSC45 insert and the '- - -' marker represents the priming sequence in λgs 1.1 complementary to residues 1135–1132. The '>' and '<' symbols represent bases involved in stems of the calculated structure for the 5' untranslated region;

FIG. 3 shows the structure of three GS expression plasmids in which a) shows plasmid pSVLGS.1 (8.5 kb) containing a 4.75 kb GS minigene under the control of the late region promoter of SV40 (L) cloned in the bacterial vector pCT54. The GS sequences include the complete coding sequence, a single intron and approximately 2 kb of 3'-flanking DNA spanning both of the presumed sites of polyadenylation, (b) shows plasmid pSV2.GS (5.5kb) containing 1.2 kb of GS cDNA under the control of the early region promoter of SV40 (E), the intron from the T-antigen gene of SV40 and a sequence containing the early region polyadenylation signal of SV40, and (c) shows plasmid pZIPGS (12.25 kb) containing the HindIII-BamHI fragment from pSV2.GS (containing the GS coding sequence and SV40 intron and polyadenylation signal) cloned in the retroviral vector pZIPIP Neo SV(X) in which latched blocks indicate irrelevant mouse DNA sequences, 5' and 3' LTRs as the long terminal repeats of Moloney Murine Leukaemia Virus (MMLV), the filled block represents an SV40 fragment spanning the origin of replication oriented such that the SV40 early region promoter directs the expression of the gene from transposon TnS which confers resistance to G418 in mammalian cells (neo) and unmarked blocks contain additional DNA sequences from MMLV;

Figure 1:
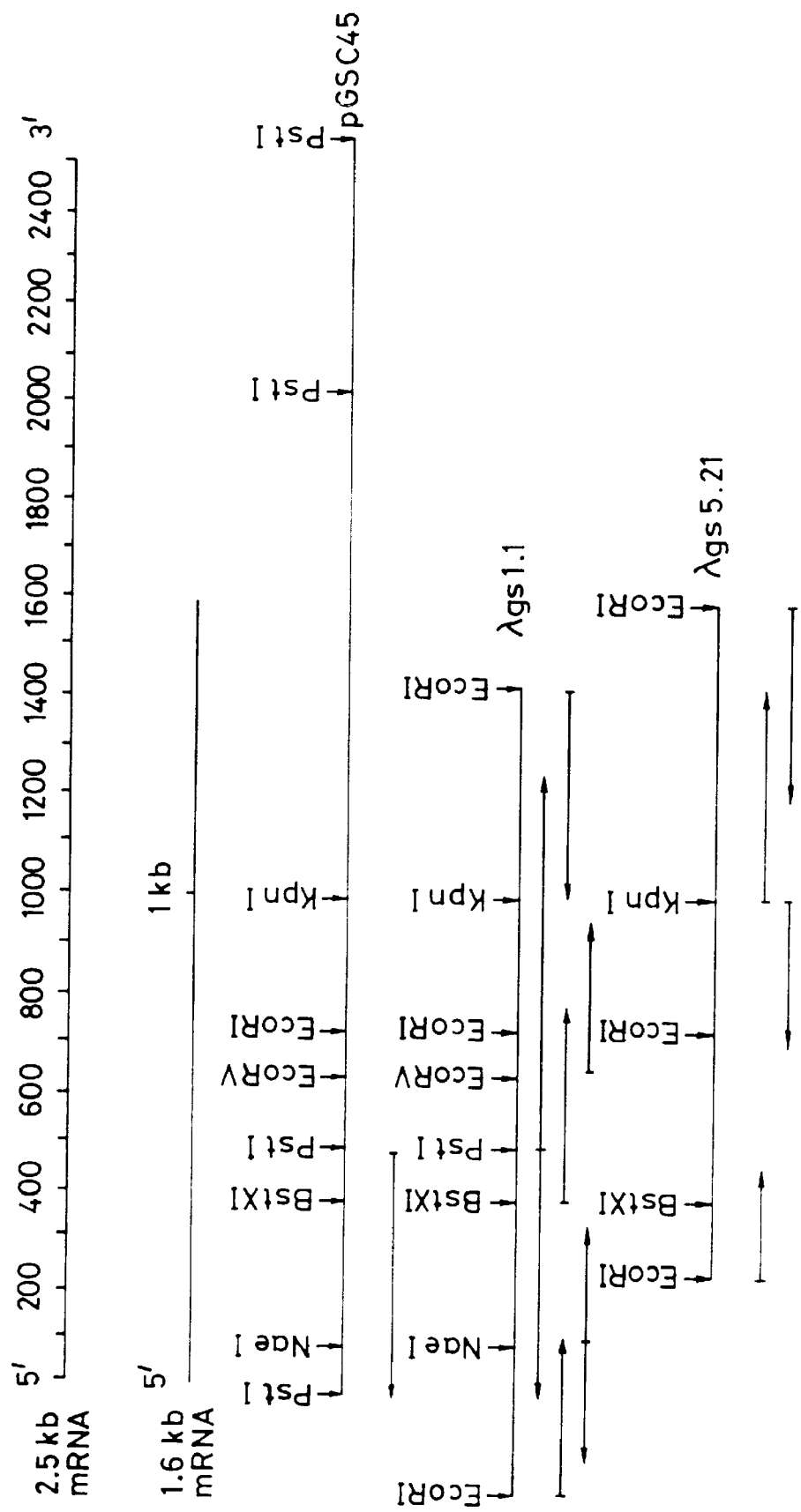
FIG. 1 shows restriction maps of the GS specific cDNA inserts in pGSC45, λgs 1.1 and λgs 5.21 clones, in which it can be seen from the arrows that the nucleotide sequence of the coding region of GS was predominantly obtained from M13 subclones of λgs 1.1 and various regions confirmed using subclones of λgs 5.21 and pGSC45.

In the nucleotide and amino acid sequences shown in the accompanying drawings and in the description, the following abbreviations are used as appropriate. U=uridine; G=guanosine; T=thymidine; A=adenosine; C=cytosine; ***=a termination codon; —denotes an unknown nucleotide residue; A=alanine; C=cysteine; D=aspartic acid; E=glutamic acid; F=phenylalanine; G=glycine; E=histidine; I=isoleucine; K=lysine; L=leucine; M=methionine; N=asparagine; P=proline; G=glutamine; R=arginine; S=serine; T=threonine; V=valine; W=tryptophan; Y=tyrosine; X=an unknown amino acid; PBS=phosphate buffered saline; SDS=sodium dodecyl sulphate; and EDTA=ethylene diamine tetraacetic acid.

EXAMPLE

Using a multi-step selection procedure in a glutamine-free medium, a mutant line was derived from the chinese hamster ovary (CHO) KG1 cell line (itself a derivative from the CHO-KI line obtained as CCL 61 from the American Type Culture Collection, Rockville, Md., USA). The mutant cell line, labelled CHO-KGIMS, is resistant to 5 mM Msx. (The parentalcell line KG1 is only resistant to 3 μM Msx).

A subclone, KGlMSC4-M, of the mutant cell line was used as a source of cellular DNA. Cells from the subclone were washed in PBS after trypsinization and pelleted at 2000 r.p.m. for 4 min. The pellet was resuspended in 100 m Tris-HCL, pH 7.5, 10 mM EDTA and lysed by the addition of SDS to 2%. RNase A was added to 50 μg/ml and the solution incubated at 37° C. for 30 min. Protease K was added to 50 μg/ml and incubation continued at 37° C. for from 30 min to 1 hr. The solution was phenol extracted twice followed by two chloroform:isoamyl alcohol (24:1) extractions. The DNA was precipitated with isopropanol and then resuspended in 2 mM EDTA, 20 mm Tris-HCl , pH 7.5 and stored at 4° C.

Genomic DNAs from parental KG1, mutants KGlMS and KGlMSC4-M, and revertant KGlMSC4-0 cells were digested with a variety of restriction endonucleases, subjected to agarose gel electrophoresis and Southern blotted onto nitrocellulose filters. These blots were probed with oligo(dT)—primed cDNA made from parental KG1 and mutant KGIMSC-4M poly(A) mRNAs. When wild-type KG1 cDNA was used as a probe, a series of identical bands was seen across tracks from all cell lines. When KGlMSC4-M mutant cDNA was used as a probe, the same common bands were seen across all tracks together with unique bands specific to mutant KGLMS and KGlMSC4-M genomic DNA. The bands common to all genomic DNAs were shown to be due to mitochondrial (mt) DNA, as determined by restriction enzyme analysis of mtDNA purified from KG1 cells. The smallest DNA fragment identified which could contain the whole of the presumptive coding sequence for GS is an 8.2-kb BglII fragment. On double digestions with Psti and Bglil, the two PstI fragments (2.1 kb and 2.4 kb) are seen to remain intact, indicating that both PstI fragments are contained within the BGlII fragment.

30 μg of KGlMSC4-M DNA was digested to completion with BglII and the fragments separated by electrophoresis on an 0.8% agarose gel. The amplified 8.2 kb band was identified using ethidium bromide staining and long wave ultra violet radiation by comparison with λ HindIII and mtPstI digests. The DNA band was eluted into a well cut into the gel and purified by phenol extraction, chloroform extraction and ethanol precipitated using carrier tRNA. Purified DNA was ligated with BamBI- digested, bacterial alkaline phosphatase-treated pUC9 (Vieira, J. and Messing, J., Gene, 19, 259–268, 1982). Recombinant DNA was used to transform E. Coli to ampicillin resistance and white colones on Xgal picked for analysis.

150 recombinant clones were obtained and DNA analysis of 11 of these showed that they all had DNA inserts of about 8.0 kb. Differential colony hybridization and DNA spot hybridizations identified two recombinant clones which gave strong hybridization with a mutant KGIMSC4-M cDNA probe but no signal with a parental KG1 cDNA probe. Both recombinants pGS1 and pGS2 produced the PstI restriction pattern expected from insertion of the required BglII restriction fragment. pGS1 DNA was used to hybrid select GS mRNA from total cytoplasmic and poly(A) KGlMSC4-M RNA. The selected MRNA was translated together with KG1 and KGlMSC4-M total cytcplasmic RNA and [$^{35}$S] methionine-labelled polypeptides separated by SDS-PAGE. The major translation product of pGS1 selected mRNA is apolypeptide of 42 000 kD MW which co-migrates with an amplified polypeptide in KGlMSC4-M translations. pGS1 therefore contains genomic CHO DNA which contains at least part of the GS gene.

This part of the work was carried out as described by Sanders and Wilson (loc. cit.).

A 3.5 kb HindIII fragment containing the 3' end of the GS gere from KGlMSC4-M was subcloned from PGS1 into pUC9 to form plasmid pG5113.

A clone bank was prepared by cloning a Sau3A partial digest of KGlMSC4-M into the BamHl site of λL47. Recombinants were selected for hybridisation to pGS1. A BamHI-EcoRI fragment from a selected λL47 recombinant was subcloned into pUC9 to form plasmid pGS2335 (Hayward et al., Nuc. Acid Res., 14, 999–1008, 1986).

cDNA libraries were made from KGlMSC4-M mRNA in pBR322 and λgt10 using standard procedures. The mRNA was converted to cDNA using oligo-dT primed reverse transcriptase, and dsDNA made by the RNase H procedure (Gubler, U. and Hoffmann, V., Gene, 25, 263–269, 1983). The dsDNA was either tailed with C residues (Michelson, A. M. and Orkin, S. H., J. Biol. Che., 257, 14773–14782, 1982), annealed to G-tailed pBR322 and transformed into E. coli DH1, or methylated and ligated to EcoRI linkers. Linkered DNA was digested with EcoRI and linkers removed by Sephadex G75 chromatography in TNES (0.14 M NaCl, 0.01 M Tris, pH 7.6, 0.001 M EDTA, 0.1% SDS). Linkered DNA in the excluded volume was recovered by ethanol precipitation and annealed to EcoRI-cut λgt10 DNA. Following in vitro packaging, recombinant phage was plated on the high frequency lysogeny strain E. coli Hfl (Huyhn, T. V., Young R. A. and Davis, R. W., in "DNA cloning techniques II: A practical approach (Ed. Glover, D. M.), I.R.L. Press Oxford, 1985). About 5000 colonies and 20000 plaques were screened on nitrocellulose filters using nick-translated probes derived from pUC subclones of GS genomic sequences. A 1 kb EcoRI-BglII: fragment from pGS2335 was used as a 5' probe, and the entire 3.5 kb HindII fragment of pGS113 was used as a 3' probe. Plasmids from positive colonies were analysed by restriction digestion of small-scale preparations of DNA and the longest clone (pGSC45) selected for further analysis.

Positive λclones were plaque purified, grown up in 5000 ml of E.coli C600 liquid culture, and the phage purified on CsCl step gradients. DNA was prepared by formamide extraction (Davis, R. W., Bostein, D. and Roth, S. R., Advanced Bacterial Genetics, Cold Spring Harbor, 1980). Clones with the longest inserts were identified by EcoRI digestion and inserts subcloned into pAT153 and M13mpll phage for further analysis and sequencing.

The colonies or plaques were screened first with a probe derived from the 5' end of the GS gene. Positive colonies or plaques from this analysis were picked and rescreened with a longer probe covering most of the 3' end of the gene. In this way it was anticipated that clones with long or possibly full length inserts would be selected and the tedious rescreening for 5' ends would be avoided. Several plasmid clones and λgt10 recombinants were derived by this means. Further analysis of one of the plasmid clones (pGSC45) by restriction enzyme digestion and partial sequencing revealed that it had an insert of about 2.8kb and a polyA sequence at the 3' end. Northern blots indicate that a major mRNA for GS is about this size (Sanders and Wilson, (loc. cit.)), so the insert in pGSC45 was potentially a full length copy of this mRNA. The two λclones ( λgs 1.1 and λgs 5.21) had inserts of 1450 bp and 1170 bp respectively. Restriction maps and alignment of the cDNA inserts in pGSC45, λgs 1.1 and λgs 5.21 are shown in FIG. 1. It is clear that the inserts in the λ clones are considerably shorter at the 3' end than the plasmid clone and may represent cDNA copies of one of the minor mRNAs. The insert in λgs.1.1 extends some 200 base pairs at the 5' end.

The nucleotide sequence of the mRNA coding for glutamine synthetase was obtained from M13 subclones of pGSC45 and EcoRI subclones of λgs 1.1 and λgs 5.21 and is shown in FIG. 2. Some confirmatory sequence was also obtained from the genomic clone pGSl. Primer extension of GS mRNA with an oligonucleotide complementary to nucleotides 147–166 gave a major extension product of 166 nucleotides. This shows that pGSC45 only lacks six or seven nucleotides from the 5' end of the mRNA. Nucleotide sequencing of the primer extended product by Maxam-Gilbert sequencing confirmed this although the first two bases could not be determined.

Sequences at the 5' end of λgs 1.1, which is some 200 bases longer at the 5' end than pGSC45, showed considerable inverted homology to sequences at the 3' end of this clone (which was about 150 bases shorter at the 3' end than λgs 5.21, (see FIG. 1). These additional sequences are probably cloning artefacts, arising during second strand syrthesis due to nucleotides 6 to 1 priming DNA synthesis via their complementarity to nucleotides 1132–1137 despite the fact that the RNase H procedure was used. It cannot be excluded that the duplication arises from transcription of a modified GS gene, producing a modified mRNA which has been subsequently cloned, although the primer extension results did not suggest that there was any major mRNA species with a 5' end longer than 166 nucleotides.

The predicted amino acid sequence for CHO glutamine synthetase is showm in FIG. 2. The $NE_2$ terminus was identified by homology with the $NH_2$ terminal peptide found in bovine brain glutamine synthetase (Johnson, R. J. and Piskiewicz, D., Biochem. Biophys. Acta, 827, 439–446, 1985). The initiating AUG follows a precise CCACC upstream consensus sequence found for true initiation codons and is followed by a purine (i.e. CCACCATGG). (Another AUG codon at position 14 is not in a favourable context by the same criteria and is followed by a termination codon in frame 21 nucleotides downstream.) The predicted amino acid composition of the GS protein gives a molecular weight of 41,964 (not allowing for N-terminal acetylation or other post-translational modifications), in agreement with other estimates. The basic nature of the protein is reflected in the excess of arginine, histidine and lysine residues over those of aspartate and glutamate.

The predicted amino acid sequence shows excellent homology with bovine and other GS derived peptide sequences obtained by peptide sequencing, indicative of an accurate DNA sequence. (The amino acid sequence allows the ordering of all the cyanogen bromide peptides and most of the tryptic peptides published for bovine GS).

The CHO sequence also shows some homology with the GS sequence from the cyanobacterium Anabaena, notably at residues 317–325, (NRSASIRIP) which are an exact match to Anabaena residues 342–350. In addition, related sequences can be found in glutamine synthetases isolated from plants.

Access to complete cDNA clones and genomic clones for Chinese hairster GS has not only allowed the amino acid sequence of glutamine synthetase to be predicted. but also allows a detailed analysis of the position of the introns within the gene and their relationship to the exons coding for the structural domains of the protein.

A GS minigene was constructed from a cDNA sequence (spanning the majority of the protein coding region) and a genomic sequence (which recreates the 3' end of the coding sequence). The 3.4 kb EcoRI-SstI fragment of pGS1 encodes a single intron, all of the 3' untranslated region of both MRNA species identified and contains about 2 kb of 3' flanking DNA. This DNA fragment was cloned between the EcoRI and BamHI sites of pCT54 (Emtage et al., PNAS-USA, 80, 3671–3675, 1983) to create pCTGS. The 0.8 kb EcoRl fragment of λgs 1.1 was then inserted at the EcoRI site of pCTGS in the correct orientation to recreate the 5' end of the gene. The late promoter of SV40 was cloned upstream by inserting the 342 bp PvuII-HindIII fragment of SV40, containing the origin of replication, at the HindIII site of the above plasmid in the appropriate orientation to produce plasmid pSVLGS-1 which is shown in FIG. 3(a)

An alternative GS expression construct was made by placing cDNA containing all of the GS coding sequences between sequences from SV40 which direct efficient expression in mammalian cells. The 1.2 kb NaeI-PvuII fragment of λgs 1.1 was cloned in place of dhfr sequences in pSV2. dhfr, (Subramani, S.,Mulligan, R. and Berg, P., Mol. Cell. Biol., 1, 854–864, 1981) between the HindIII and BglII sites to form pSV2.GS which is shown in FIG. 3(b).

In order to place GS coding sequences under the cortrol of the Moloney murine leukaemia virus (MYLV) LTR promoter, the HindII-BamHI fragment fromr pSV2.GS (see FIG. 3b) was introduced at the BamHI site of pZIP-NeopSV (X) (Cepko, C. L., Roberts, B. E. and Mulligan, R. C., Cell, 37, 1053–1062, 1984).

The 3.0 kb HindIII-BamHI fragment of ptPA 3.16 (Stephens, P. E., Bendig, M. M. and Hentschel, C. C., manuscript in preparation) contains a cDNA coding for tissue plasminogen activator, downstream of which is the SV40 small t-intron and the polyadenylation signal from the early region transcript of SV40. This fragment was cloned in a 3-way ligation with the 342 bp SV40 PvuII-BindIII fragment into the BamHl site of pSVLGS.1 so that the tPA gene was under the control of the SV40 early promoter. This generated two plasmids, pSVLGStPA16, in which the GS and tPA transcription units are in tandem and pSVLGStPA17, in which the two genes are in opposite orientations.

CHO-KI cells, obtained from ATCC, were grown in Glasgow modified Eagle's medium (GMEM) without glutamine and supplemented with 10% dialysed foetal calf serum (GIBCO), 1 mM sodium pyruvate, non-essential amino acids (alanine, aspartate, glycine and serine at 100 $\mu$M, asparagine, glutamate and proline at 500 $\mu$M) and nucleosides (adenosine, guanosine, cytidine and uridine at 30 $\mu$M and thymidine at 10 $\mu$M). For selection, L-methionine sulphoximine (Msx from Sigma) was added at appropriate concentrations. Approximately $3\times10^6$ cells per 100 mm petri dish were transfected with 10 $\mu$g circular plasmid DNA according to the calcium phosphate co-precipitation procedure (Graham, F. L. and van der Eb, A. J., Virology, 52, 456–467, 1983). Cells were subjected to a glycerol shock (15% glycerol in serum-free culture medium for 2 minutes) 4 hours after transfection (Frost, E. and Williams, J. Virology, 91, 39–50, 1978). One day later, transfected cells were fed with fresh selective medium and colonies of surviving cells were visible within 2–3 weeks.

tPA activity in cell culture supernatants was measured using a fibrin-agarose plate assay using a tPA standard (Biopool) for comparison. Attached cells were typically washed in serum-free medium and incubated for 18–20 hours in serum-free medium at 37° C. After removal of medium samples for assay, the cells were trypsinised and viable cells counted. Results were then expressed as units of tPA/$10^6$cells/24 hours. Colonies of cells in petri dishes were assayed for tPA production by overlaying directly with a fibrin agarose gel.

In the glutamine-free medium used in these experiments, the specific GS inhibitor, Msx is toxic to CHO-KI cells at concentrations above 3 $\lambda$M. To test whether the GS expression plasmids could synthesise functional GS in vivo, each plasmid was introduced into CHO-KI cells by calcium phosphate-mediated transfecton and tested for the ability to confer resistance to higher concentrations of Msx.

Resistance to Msx can, however, also arise by amplification of the endogenous GS genes (or perhaps by other unknown mechanisms). Therefore, in order for a GS expression vector to be useful as a dominant selectable marker, it must confer resistance to a particular concentration of Msx with a greater frequency than the frequency of spontaneous resistant mutants. The frequency with which spontaneously resistant clones are detected depends on the concentration of Msx used for selection. Thus, for instance gene amplification in CHO-KI cells leads to approximately 1 surviving colony/$10^4$ cells plated in 10 $\mu$M Msx, but this frequency declines to less than $1/10^7$ if cells are selected for resistance to 25 $\mu$M Msx.

Since the frequency of transfection of CHO cells using the calcium phosphate co-precipitate technique is generally reported to be less than $1/10^3$, a range of Msx concentrations was chosen for selection in excess of 10 $\mu$M. The results in Table 1 show that transfection with any of the three GS expression plasmids leads to survival of a greater number of Msx-resistant colonies than the background frequency detected in mock-transfected cells when selected at 15 $\mu$M or 29 $\mu$M Msx.

pZIPGS yields only a slight increase in the number of surviving colonies above background. This vector would therefore be a poor selectable marker and was not studied further. pSV2.GS and pSVLGS.1, however, both appear to act as effective dominant selectable markers in this cell line. The frequency with which resistant colonies arise after transfection with either plasmid in these experiments is at least 25 times the frequency due to endogenous amplification if selection is carried out at 15–20 $\mu$M Msx. Apparent transfection frequencies for pSV2.GS of up to $3.8/10^5$ cells and for pSVLGS.1 of up to $2.5/10^5$ cells were observed. The differences in apparent transfection frequencies between the three plasmids are likely to reflect differences in he efficiency with which the GS gene is expressed in the above three vectors.

An independent estimate of transfection efficiency can be obtained in the case of pZIPGS since the vector also contains a neo gene which confers resistance to the antibiotic G418. Selection with G418 instead of Msx yielded a transfection frequency substantially higher than obtained by selection in 14–20 $\mu$M Msx (see Table 1), indicating that the vector is being taken up by the cells and reinforcing the view that the GS gene is relatively poorly expresses in this vector.

TABLE 1

Apparent transfection frequencies of constructs in CHO-K1 cells were determined by the number of surviving colonies/$10^6$ transfected cells at various concentrations of Msx, or by resistance to 0.8 mg/ml G418 (Results are from 3 transfections, (i), (ii) and (iii)).

| Vector | 15 $\mu$M | 20 $\mu$M | 25 $\mu$M | 30 $\mu$M | 100 $\mu$M | 1 mM | G418 |
|---|---|---|---|---|---|---|---|
| pSVLGS.1 | | | | | | | |
| (i) | 13.6 | 9.2 | 5.6 | 2.4 | 0.24 | 0 | — |
| (iii) | — | 24.5 | 10.0 | — | — | — | — |
| pSV2.GS | | | | | | | |
| (i) | 26.4 | 18.0 | 12.0 | 12.0 | 1.4 | 0 | — |
| (ii) | — | 32.0 | 7.4 | — | — | — | — |
| (iii) | — | 38.0 | 29.0 | — | — | — | — |
| pZIPGS | | | | | | | |
| (i) | 0.72 | 0.5 | 0 | 0 | 0 | 0 | — |
| (ii) | — | 1.1 | 0 | — | — | — | 30 |
| Mock | | | | | | | |
| (i) | 0.47 | 0.24 | 0 | 0 | 0 | 0 | 0 |
| (ii) | — | 0.29 | 0 | — | — | — | 0 |
| (iii) | — | 1.0 | 0 | — | — | — | — |

In order to confirm that the generation of Msx-resistant colonies is due to expression of transfected GS genes, rather than to some non-specific effect of the input DNA, there are three predictions which can be tested. Firstly, the Msx-resistant cells should contain vector DNA. Secondly, novel GS mRNAs should be produced in these cell lines, since the heterologous promoters used will direct the formation of GS mRNAs which differ in length at the 5' end from the natural GS mRNA. Thirdly, active transfected GS genes should be amplifiable by selection in increased concentration of Msx. These predictions were therefore tested as follows.

Three cell lines were established from individual colonies arising after transfection with pSVLGS.1 and three cell lines from colonies transfected with pSV2.GS. Cell lines SVLGS 2 and SVLGS 5 are resistant to 20 μM Msx and SVLGS 9 to 30 μM Msx. Cell lines SV2.GS20, SV2.GS25, and SV2.GS30 are resistant to 20, 25 and 30 μM Msx respectively.

Figure 4A:
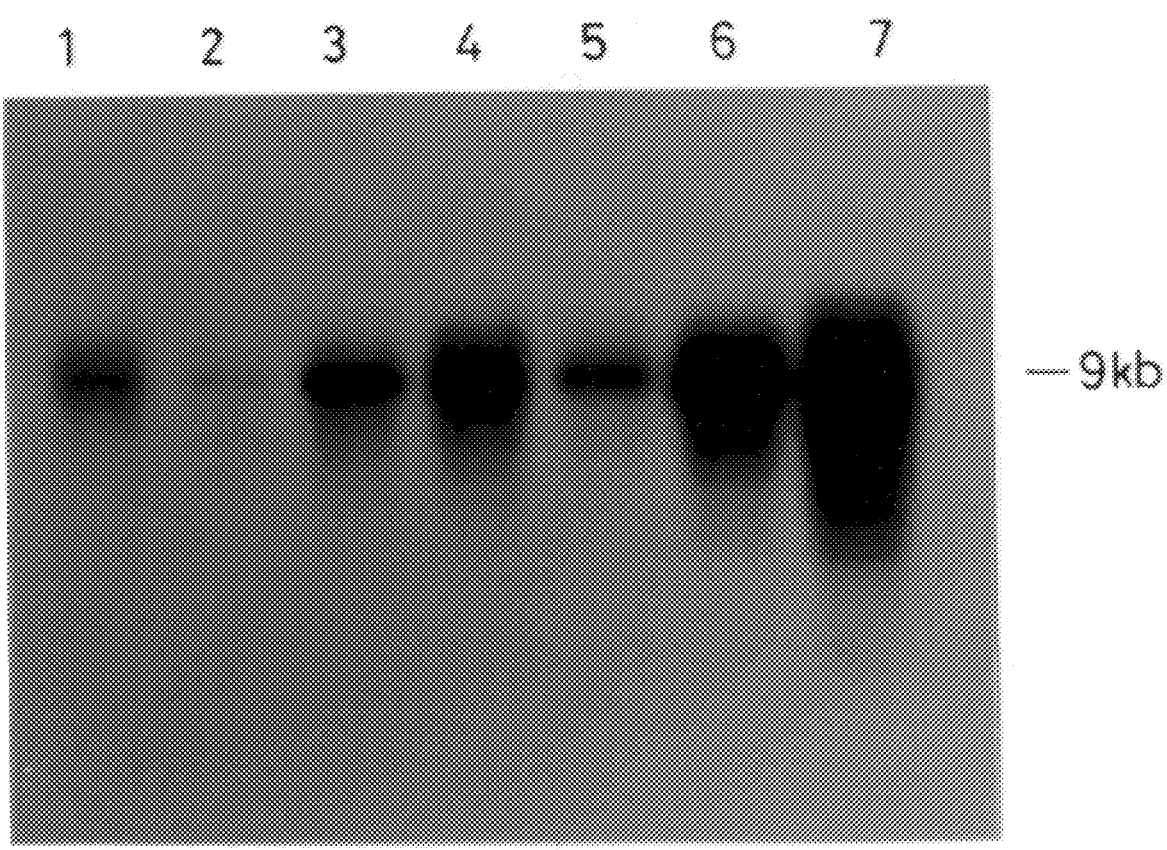
FIG. 4 shows Southern blots of cell lines transfected with pSVLGS.1 (Panel A) or pSV2 GS (Panel B). The blot is probed with an RNA probe specific for SV40 origin-region DNA. Panel A represents a 2 hour exposure. Each lane contains 2.5 μg genomic DNA from the following cell lines. Lanes 1 to 3 contain DNA from initial transfectants: lane 1, SVLGS2; lane 2, SVLGSS; lane 3, SVLGS9. Lanes 4 to 6 contain DNA from cell lines obtained after a single round of selection for gene amplification with Msx: lane 4 SVLGS2 (500 μMR); lane 5, SVLGS5(250 μMR); lane 6, SVLGS9 (500 μMR ). Lane 7 contains DNA from a cell line subjected to 2 rounds of selection for gene amplification, SVLGS5(2 mMR). Panel B is an exposure of approximately two weeks. Each of lanes 1 to 6 contain 5 μg of genomic DNA and lane 7 contains 2.5 μg. Lanes 1 to 3 contain DNA from initial transfectant cell lines: lane 1, SV2 GS20; lane 2, SV2.GS25; lane 3, SV2 GS30. Lanes 4 to 6 represent cell lines after one round of selection in higher concentrations of Msx: lane 4, SV2.GS20(100 μMR); lanes SV2.GS25(500 μMR); lane 6, SV2.GS30(500 μMR). Lane 7 represents a cell line obtained after two rounds of selection in Msx, SV2.GS30(10 MR).

DNA was prepared from each of these cell lines and a Southern blot of the DNA samples was hybridised with an RNA probe specific for SV40-ORI region DNA. The result, shown in FIG. 4, indicates that all of the Msx-resistant cell lines contain vector DNA. The number of copies of the vector present in each cell can be estimated by comparison with known amounts of a standard preparation of vector DNA, loaded on the same gel. From this, it is clear that all of the SVLGS cell lines contain multiple copies of the vector up to about 500 copies per cell (see Table 2). All of the SV2.GS cell lines also contain vector DNA but in all three cases there seems to have been integration of only a single copy of vector DNA per cell.

It is to be noted that the result obtained with pSVLGS.1 is highly unexpected. Up until the present there has been no reported case in which such a high copy number has been produced merely by transfection. It is believed that this high copy number is due to the presence in the vector of a DNA sequence which favours the incorporation of high numbers of copies of vector DNA into the host cell's DNA.

Such high copy numbers of integrated vectors have not been observed with pSV2.GS. It is therefore believed that DNA sequences partly responsible for the high copy number transfection are found either in the intron or in the 3' region of the genomic GS DNA part of the pSVLGS.1 vector or adjoining vector sequences. Bowever, the copy number probably also reflects the expression level required to attain resistance to the particular level of Msx used for selection.

Clearly, this high copy number transfection sequence will be of use not only with GS encoding sequences but also with other protein sequences, such as those encoding selectable markers or amplifiable cenes because it provides a means of increasing copy number and hence expression levels of desired genes additional to the effects of selection for further gene amplification.

Therefore according to a further aspect of the invention there is provided the recombinant DNA sequence present in the pSVLGS.1 vector which is responsible for achieving high copy number transfection of vector DNA into a host cell or any other recombinant DNA sequence which will provide the same function.

The 5' ends of GS mRNA produced by Msx-resistant cell lines were analyzed by primer extension analysis. A synthetic oligomer 19 bases in length was synthesised which hybridises to a region of the MRNA near the start of the protein coding region. Reverse transcriptase should extend this primer to a length of 146 bps from wild type GS mRNA and to a length of approximately 400 bps to the start of transcription in the case of pSVLGS.1 mRNA, The RNA predicted from pSV2.GS is shorter than the natural mRNA and so could be masked by "drop-offs" in the primer extension reaction and was not analysed.

Figure 5:
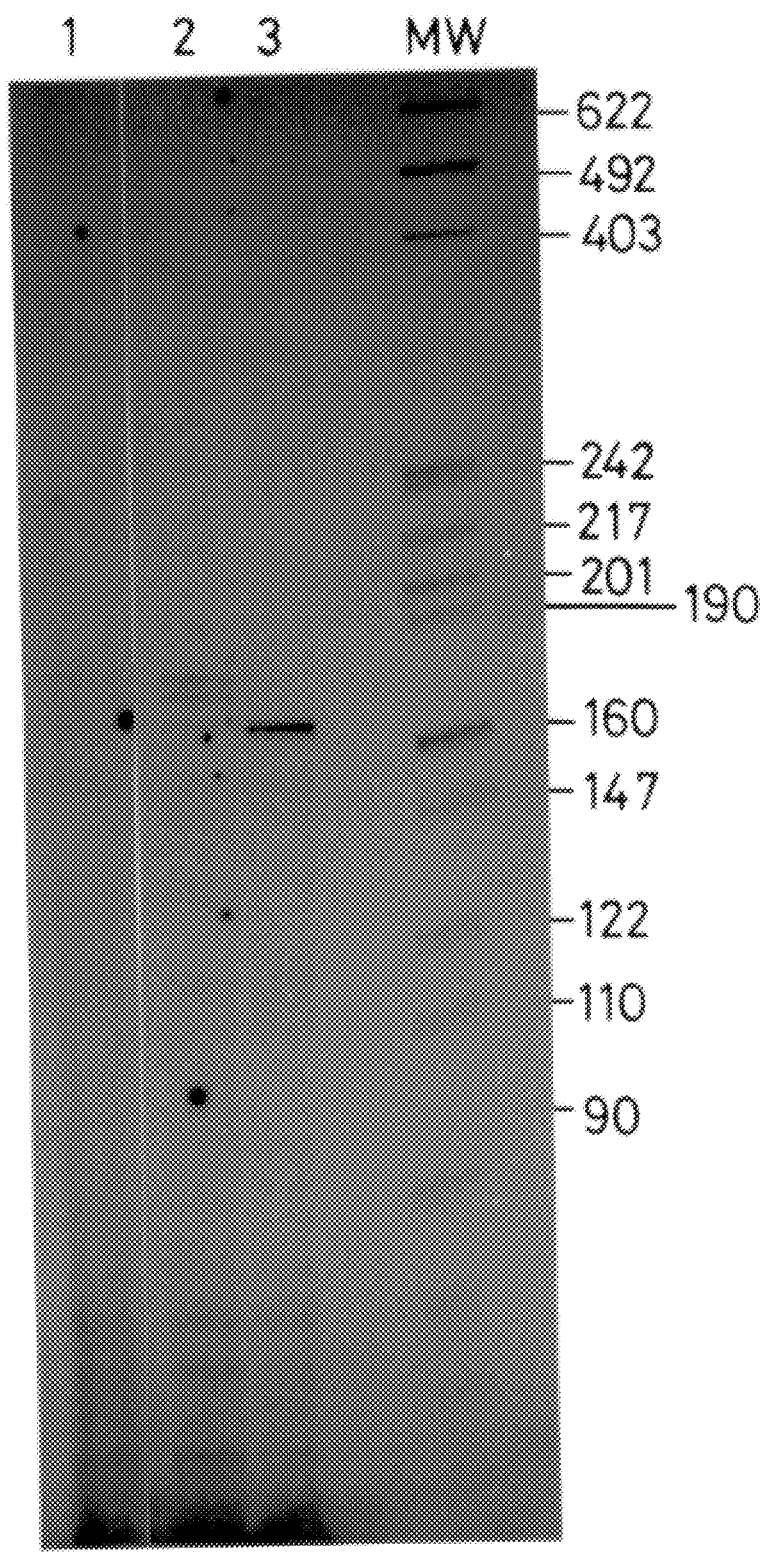
FIG. 5 shows a primer extension analysis of RNA derived from cell lines transfected with pSVLGS.1. A DNA oligonucleotide which binds to RNA at the presumed translation "start" was used to synthesise DNA from total RNA preparations. RNA preparations shown are: lane 1, SVLGS2; lane 2, SVLGS5; lane 3 a derivative of CHO-KI resistant to 30 μM Msx to indicate the extension from wild-type GS mRNA); MW, pAT153 digested with Hpall molecular weight markers.

The results shown in FIG. 5 show that a GS specific mRNA longer than wild-type mRNA is indeed produced in SVLGS cell lines, strongly supporting the conclusion that the transfected gene is transcribed in these cells. The reverse transcriptase does not extend the primer to the predicted length, but seems to drop off at at least 3 major sites, probably due to inhibition of reverse transcription by secondary structure in the 5' untranslated region of this RNA.

Three Msx-resistant cell lines transfected with pSVLGS.1 and three cell lines transfected with pSV2.GS were grown in various concentrations of Msx in crder to select for GS gene amplification. For each cell line, approximately $10^5$ cells were plated in 100 μM, 250 μM, 500 μM and 1 mM Msx. After 12 days, the maximum concentrations of Msx at which surviving colonies could be observed in each cell line were as follows: SVLGS2, 500 μM; SVLGS5, 250 μM; SVLGS9, 500 μM; SV2.GS20, 100 μM; SV2.GS25, 500 μM; and SV2.GS30, 500 μM. The most highly resistant colonies obtained from each cell line were pooled and two of these Msx-resistant pools were subjected to a second round of amplification. SVLGS2 (500 μMR) and SV2.GS30 (500 μMR) were plated out at 1 mM, 5 mM, 10 mM and 20 mM Msx. After 15–20 days, colonies appeared on plates containing SVLGS2(500 μMR) at up to 2 mM Msx and in the case of SV2.GS (500 μMR) at up to 10 mM Msx. From these, two highly resistant cell lines SVGS2 (2 mMR) and SV2.GS30 (10 mMR) were established. Each of these highly resistant cell lines contain cells which have arisen from multiple independent amplification events.

A Southern blot of DNA prepared from all of the Msx-resistant cell lines was hybrised with a probe specific for SV40 ORI-region DNA. The results of this are shown in FIG. 3. From a comparison with standard preparations of plasmid DNA, the copy numbers could be determined and these are shown in Table 2.

After the first round of selection, all three SVLGS cell lines show approximately a 10-fold increase in copy number of the vector DNA.

TABLE 2

Copy Number of Transfected Genes Subjected to Selection for gene amplification

| Cell Line | Conc. of Msx (μM) | Copy Number |
|---|---|---|
| SVLGS2 | 20 | 170 |
| SVLGS5 | 20 | 25 |
| SVLGS9 | 30 | 500 |
| SVLGS2 (500 μMR) | 500 | 1200 |
| SVLGS5 (250 μMR) | 250 | 300 |
| SVLGS9 (500 μMR) | 500 | 4200 |
| SVLGS2 (2 mMR) | 2000 | 15000 |
| SV2.GS20 | 20 | 1 |
| SV2.GS25 | 25 | 1 |
| SV2.GS30 | 30 | 1 |
| SV2.GS20 (100 μMR) | 100 | 1 |
| SV2.GS25 (500 μMR) | 500 | 1 |
| SV2.GS30 (500 μMR) | 500 | 1 |
| SV2.GS30 (10 mMR) | 1000 | 5–10 |

In the second round of selection, SVLGS2 shows at least a further 10 fold amplification attaining approximately 15,000 copies/cell.

In marked contrast, the single copy of pSV2.GS present in initial transfectants is not significantly increased after a single round of selection and SV2.GS30 (10 mMR) resistant to 10 mM Msx contains only 5–10 copies of the vector in each cell.

In order to determine whether there has also been amplification of the endogenous GS genes, the probe was removed and the blot re-probed with a nick-translated BglI-BglII DNA fragment obtained from the third intron of the GS genomic sequences. This probe is therefore specific for endogeneous GS genes and does not hybridise with the transfected genes which lack this intron. No significant endogenous gene amplification could be detected by this means in SVLGS cell lines A small degree of endogenous amplification could be seen in SV2.GS30 (10 mMR) cell DNA.

Thus pSV2.GS, while acting as an effective dominant selectable marker in CHO-KI cells, appears to express GS too efficiently to be suitable as an amplifiable marker, since very high levels of Msx are required in order to select for even slightly increased copy number. pSVLGS.1 on the other hand can be used as a dominant selectable marker and can also be amplified to very high copy numbers.

The suitability of pSVLGS.1 as a selectable and amplifiable vector was tested by introducing into it a transcription unit capable of expressing tissue-plasminogen activator (tPA). Two plasmids were examined in which tPA cDNA under the control of the SV40 early region promoter and polyadenylation signal was clonea at tne unique bamHI site of pSVLGS.1. In pSVLGS.tPA16, the GS and tPA genes are in the same orientation and in pSVLGS.tPA17, the two genes are in opposite orientations.

Both constructions were introduced into CHO-KI cells and transfected cells were selected for resistance to 15 $\mu$M Msx. After 10 days, the surviving colonies were screened for tPA activity by fibrin overlays. Many of the surviving colonies secreted tPA, thus confirming that the GS gene could act as a selectable marker to identify transfected clones. The tPA-induced clearings in the fibrin gel were larger and more numerous on plates transfected with pSVGS.tPA16, indicating that the tPA gene was more efficiently expressed when in the same orientation in the vector as the GS gene than when the two genes were in opposite orientations. 10 colonies from a transfection with pSVLGS.tPA16, which produced large tPA clearings, were grown in 96-well plates. Of these, the two cell lines secreting the highest levels of tPA, 16–1.20 $\mu$MR and 16–2.20 were selected for further study. Each was subjected to selection in increased concentrations of Msx and the tPA production from pools of colonies obtained at different stages is shown in Table 3.

TABLE 3

| Cell line | tPA secreted (U/10$^6$ cells/24 hours) |
|---|---|
| 16-1.20 $\mu$MR | 260 |
| 16-1.200 $\mu$MR | 2700 |
| 16-2.20 $\mu$MR | 400 |
| 16-2.200 $\mu$MR | 2750 |
| 16-2.10 mMR | 4000 |

16–2.10 mMR, the cell line producing the highest levels of tPA, was cloned by limiting dilution and a clone was isolated which secreted 4000 U/10$^6$ cells/day. This level is comparable with the highest level of tPA expression reported using DHFR co-amplification.

It has thus been shown that, when a GS cDNA cloned in the retrovirus based vector pZIP-Neo SV(X) was used, the frequency with which Msx-resistant colonies arose was low, probably due to relatively inefficient expression from this vector in this cell line. On the other hand, two different constructs in which the GS gene was under the control of SV40 promoters gave rise to cells resistant to substantially higher levels of Msx than wild-type cells. All of the resistant colonies tested contained vector DNA, and novel GS mRNAs consistent with transcription of the transfected genes could be detected in cell lines containing pSVLGS.1 DNA. Msx-resistant colonies could be identified using both GS expression plasmids using SV40 promoters at a frequency greater than 1/10$^5$ cells, indicating that both constructs could be useful as dominant selectable markers for the introduction of cloned DNA into CHO-KI cells.

The expression plasmid pSVLGS.1 containing a GS minigene utilising its own RNA processing signals and under the control of an SV40 late promoter, can unexpectedly be used to introduce a high number of copies of the vector into each transfected cell.

Both GS genes under the control of SV40 promoters were capable of further amplification when transfected cell lines were selected in higher concentrations of msx. Cell lines expressirg pSV2.GS yielded variant clones resistant to very high levels of Msx (up to 65 times higher than originally used to select transfectants) with an increase in copy number to only 5–10 per cell. There was little detectable concomitant amplification of endogenous genes.

pSVLGS.1 is a much more suitable aimplifiable vector since the increase in copy number was roughly proportional to the concentration of Msx and very high copy numbers were achieved (approximately 10,000 copies per cell in cells resistant to 2 mM Msx). In this case, no detectable endogenous gene amplification occurred.

The pSVLGS.1 amplifiable vector has been used to introduce a tPA gene into CHO-KI cells and it has been shown that gene amplification leads to higher levels of tPA expression. Variant clones resistant to ten times the concentration of Msx of the original transfectants secrete about ten times the amount of tPA, but a further 50 fold increase in Msx-resistance led to less than a 2 fold increase in tPA secretion. This suggests that some aspect of the synthesis or secretion of tPA is close to saturation in these highly Msx-resistant cells. The maximum level of tPA secretion of 4000 U/10$^6$ cells/day in the 16–2.10 mMR cell line is comparable with the levels of expression previously observed in dhfr CHO cells using DHFR-mediated gene amplification, the highest reported level of secretion being 6000 U/10$^6$ cells/day. This also supports the conclusion that tPA secretion is close to the maximum attainable by current methods in these cells.

It will be appreciated that the present invention is described above purely by way of illustration and that modifications and variations thereof may be made by the person skilled in the art without departing from the spirit and scope thereof as defined in the appended claims.

We claim:

1. A recombinant DNA expression vector which is amplifiable in a transformed host cell and which encodes the complete amino acid sequence of a mammalian glutamine synthetase (GS).

2. A host cell transformed with a vector according to claim 1.

3. A recombinant DNA expression vector according to claim 1, wherein the mammalian glutamine synthetase (GS) has the amino acid sequence of the chinese hamster GS of FIGS. 2a to 2d.

4. A vector comprising a gene which encodes the complete amino acid sequence of a glutamine synthetase (GS) and a gene which encodes the amino acid sequence of a desired protein other than said GS.

5. A method of co-amplifying a recombinant DNA sequence which encodes the complete amino acid sequence of a desired protein other than a glutamine synthetase (GS), comprising:

(a) transforming a eukaryotic host cell with the expression vector of claim 4; and (b) culturing said transformed host cell under conditions which allow transformants containing an amplified number of copies of the vector to be selected.

6. Plasmid pSVLGS.tPA16.

7. Plasmid pSVLGS.tPA17.

8. An expression vector for co-amplifying a recombinant DNA which encodes the amino acid sequence of a desired protein other than a glutamine synthetase (GS) comprising:

(a) a recombinant DNA which encodes the complete amino acid sequence of a GS; and (b) a recombinant DNA which encodes the complete amino acid sequence of a desired protein other than said GS, wherein the GS and desired protein coding DNAs are linked such that amplification of the GS coding sequence results in co-amplification of the desired protein coding DNA.

9. An amplifiable recombinant DNA which encodes a complete, enzymatically active glutamine synthetase (GS).

10. A host cell transformed by a recombinant DNA expression vector according to claim 3.

11. The method of claim 5, wherein step (b) comprises culturing the transformed host cell in media containing a GS inhibitor and selecting for transformed cells which are resistant to progressively increased levels of the GS inhibitor.

12. The method of claim 11, wherein the GS inhibitor is selected from the group consisting of phosphinothricin and methionine sulphoxime.

* * * * *